(12) United States Patent
Spalding et al.

(10) Patent No.: US 10,126,164 B2
(45) Date of Patent: Nov. 13, 2018

(54) FLAME SENSING

(71) Applicant: General Electric Company, Schenectady, NY (US)

(72) Inventors: Michael Charles Spalding, Hudson, OH (US); Kenneth Keith Lambach, Monroe Falls, OH (US)

(73) Assignee: General Electric Company, Schenectady, NY (US)

( * ) Notice: Subject to any disclaimer, the term of this patent is extended or adjusted under 35 U.S.C. 154(b) by 348 days.

(21) Appl. No.: 14/818,358

(22) Filed: Aug. 5, 2015

(65) Prior Publication Data
US 2017/0038251 A1 Feb. 9, 2017

(51) Int. Cl.
*G01J 1/42* (2006.01)
*G01J 1/02* (2006.01)
*G01J 1/08* (2006.01)
*G01N 21/94* (2006.01)
*F23N 5/08* (2006.01)
*G01J 5/08* (2006.01)
*G01J 5/00* (2006.01)
*G01J 5/04* (2006.01)
(Continued)

(52) U.S. Cl.
CPC .............. *G01J 1/429* (2013.01); *F23N 5/082* (2013.01); *G01J 1/0228* (2013.01); *G01J 1/08* (2013.01); *G01J 5/0018* (2013.01); *G01J 5/026* (2013.01); *G01J 5/042* (2013.01); *G01J 5/0875* (2013.01); *G01J 5/0896* (2013.01); *G01N 21/94* (2013.01); *F23N 2029/06* (2013.01); *G01N 2021/157* (2013.01); *G01N 2201/062* (2013.01); *Y02T 50/677* (2013.01)

(58) Field of Classification Search
CPC .......... G01J 1/429; G01J 5/026; G01J 5/0018; G01J 5/0875; G01J 5/0896; G01J 5/042; G01J 1/08; G01J 1/0228; F23N 5/082; G01N 21/94; G01N 2021/157; G01N 2201/062
USPC ......................................................... 250/372
See application file for complete search history.

(56) References Cited

U.S. PATENT DOCUMENTS 6,078,050 A * 6/2000 Castleman ........... G08B 25/002
    250/339.15
6,153,881 A * 11/2000 Castleman ............. G08B 17/12
    250/339.14
(Continued)

*Primary Examiner* — David Porta
*Assistant Examiner* — Gisselle Gutierrez
(74) *Attorney, Agent, or Firm* — Mintz Levin Cohn Ferris Glovsky and Popeo, P.C.

(57) ABSTRACT

A flame sensor detects the presence of a flame in a combustion system in which the flame emits light. The flame sensor includes a body connectable with the combustion system. A photodetector is supported in the body. The photodetector responds to light emitted by the flame and generates an electrical signal proportional to an intensity of the light. A window is supported in the body and located between the combustion system and photodetector. The window is susceptible to contamination from the combustion system and the contamination may decrease sensitivity of the photodetector. A light source is supported in the body. The light source emits light so that a predetermined amount of the light emitted by the light source reflects into the photodetector when contamination is present on the window and the photodetector generates a signal indicative of contamination on the window.

18 Claims, 4 Drawing Sheets

(51) Int. Cl.
*G01J 5/02* (2006.01)
*G01N 21/15* (2006.01)

(56) References Cited

U.S. PATENT DOCUMENTS

| | | | | |
|---|---|---|---|---|
| 6,515,283 | B1* | 2/2003 | Castleman | G08B 17/12 |
| | | | | 250/339.15 |
| 6,518,574 | B1* | 2/2003 | Castleman | G08B 17/12 |
| | | | | 250/339.05 |
| 6,940,554 | B2 | 9/2005 | Robins | |
| 7,948,628 | B2* | 5/2011 | Laluvein | G01J 1/04 |
| | | | | 356/445 |
| 9,459,142 | B1* | 10/2016 | Huseynov | G08B 17/12 |
| 2009/0015824 | A1* | 1/2009 | Shubinsky | G01N 21/94 |
| | | | | 356/237.3 |
| 2011/0309248 | A1* | 12/2011 | Thoma | G01J 1/0407 |
| | | | | 250/339.06 |
| 2013/0273483 | A1 | 10/2013 | Spalding | |
| 2013/0318994 | A1* | 12/2013 | Hoffman | F23M 11/045 |
| | | | | 60/779 |
| 2014/0112537 | A1* | 4/2014 | Frank | H04N 5/33 |
| | | | | 382/103 |
| 2016/0061747 | A1* | 3/2016 | Lee | G01N 21/94 |
| | | | | 356/73 |
| 2017/0205278 | A1* | 7/2017 | Liang | G01J 1/0414 |

* cited by examiner

FLAME SENSING

BACKGROUND

In combustion systems, such as gas turbines, furnaces, boilers and internal combustion engines, it is desirable to know if combustion is occurring. Because of the location or noisy environment that the combustion system may be operating in, it may be difficult to determine the presence or absence of combustion.

For example, in an oil or gas fueled turbine, fuel is fed into a combustion chamber within which an ignition flame is present. If the flame becomes extinguished, commonly referred to as a flame-out condition, it is a concern that fuel may continue to be fed into the hot combustion chamber without appropriate ignition. Damage to the turbine can occur if the fuel is then inappropriately ignited (e.g., ignition caused by something other than the ignition flame). Consequently, if the ignition flame is extinguished within the combustion chamber, it is important that the fuel feed into the combustion chamber is quickly terminated and, thus, limit non-combusted fuel build up.

A flame sensor is generally used for detecting the presence or absence of an ignition flame within a combustion chamber of a gas turbine. In a flame sensor, a photodiode or other sensing element can be positioned inside the flame sensor. Light from the flame can travel through a window and be focused by a lens onto the photodiode. The output of the photodiode is generally proportional to the intensity of the light that the photodiode detects.

Sensitivity of the flame sensor is often diminished by contamination on the outside of a sapphire window filtering or attenuating light from the flame. This attenuation can be indistinguishable from malfunction of the flame sensor itself or of a flame-out condition. Contamination such as ash, dust, sand, water, or large pieces of refractory can deposit on the window and block the light from entering the flame sensor.

SUMMARY

It could be advantageous to have a feature that tells the operator if lowered sensitivity is due to contamination. This feature could be a valuable troubleshooting/diagnostic tool.

The following summary presents a simplified summary in order to provide a basic understanding of some aspects of the arrangements and/or methods discussed herein. This summary is not an extensive overview of the arrangements and/or methods discussed herein. This summary is also not intended to identify key elements or to delineate the scope of such arrangements and/or methods. The sole purpose of this summary is to present some concepts in a simplified form as a prelude to the more detailed description that is presented later. This summary is not intended to be used to limit the scope of the claimed subject matter and other embodiments are possible.

This disclosure relates generally to a sensor for detecting the presence of a flame in a combustion system. In particular, the disclosure relates to an improved flame sensor, system and method for determining the presence of a flame in a combustion system that may have components contaminated by combustion by-products.

A flame sensor, according to one aspect of the disclosed subject matter, detects the presence of a flame in a combustion system in which the flame emits electromagnetic radiation. The flame sensor includes a body disposed proximate to the combustion system. The flame sensor includes a photodetector supported in the body. The photodetector is configured to generate an electrical signal proportional to an intensity of electromagnetic radiation. The flame sensor includes a window supported in the body and located between the combustion system and the photodetector. The flame sensor includes a source supported in the body. The source emits electromagnetic radiation toward the window, wherein at least some of the electromagnetic radiation emitted by the source reflects back toward the photodetector when contamination is present on the window.

A system, according to another aspect of the disclosed subject matter, includes a combustion source in which a flame may be generated and in which the flame emits electromagnetic radiation. The system includes a sensor for detecting the presence of the flame in the combustion source. The flame sensor includes a body disposed proximate to the combustion system. The flame sensor includes a photodetector supported in the body. The photodetector is configured to generate an electrical signal proportional to an intensity of electromagnetic radiation. The flame sensor includes a window supported in the body and located between the combustion system and the photodetector. The flame sensor includes a source supported in the body. The source emits electromagnetic radiation toward the window, wherein at least some of the electromagnetic radiation emitted by the source reflects back toward the photodetector when contamination is present on the window. The system includes a modulator to modulate the source by varying the electromagnetic radiation emitted by the source to a predetermined pattern so the electromagnetic radiation sensed by the photodetector can be distinguished between the electromagnetic radiation emitted by the source and the electromagnetic radiation emitted by the flame.

A method, according to yet another aspect of the disclosed subject matter, detects contamination on a flame sensor window. The method includes the step of providing a flame sensor for detecting the presence of a flame in a combustion system in which the flame emits electromagnetic radiation. The flame sensor includes a body disposed proximate to the combustion system. The method includes the step of supporting a photodetector in the body. The photodetector detects the electromagnetic radiation. The photodetector is configured to generate an electrical signal proportional to an intensity of the electromagnetic radiation emitted by the flame. The method includes the step of supporting a window in the body and locating the window between the combustion system and the photodetector. The method includes the step of supporting a source in the body. The source emits electromagnetic radiation toward the window. The method includes the step of passing a first predetermined amount of the electromagnetic radiation emitted by the source through the window when there is no contamination on the window. The method includes the step of reflecting a second predetermined amount of the electromagnetic radiation emitted by the source in a direction towards the photodetector when there is contamination on the window. The method includes the step of detecting with the photodetector the second predetermined amount of the electromagnetic radiation emitted by the source and communicating a signal indicative of contamination on the window.

DESCRIPTION OF THE DRAWINGS

The following description and drawings set forth certain illustrative embodiments, aspects and implementations. These are indicative of but a few of the various ways in which one or more aspects may be employed. Further features will become apparent to those skilled in the art from reading the following description with reference to the accompanying drawings, in which.

DETAILED DESCRIPTION

Figure 1:
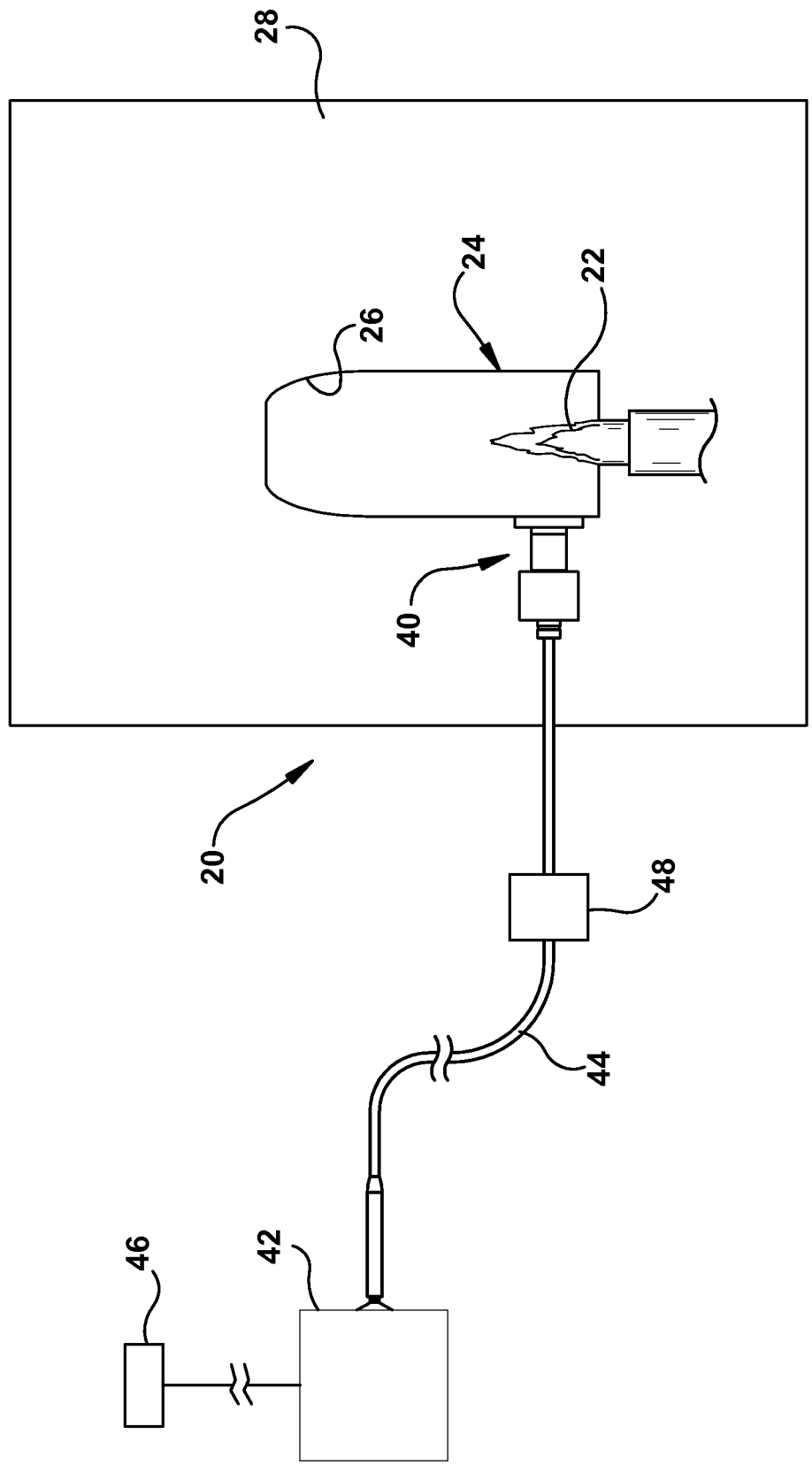
FIG. 1 is an overall schematic illustration of in an example combustion system incorporating a flame sensor system, according to one aspect of the disclosed subject matter.

The disclosed subject matter is directed to using electromagnetic energy (e.g., light) from a source to check if there is contamination (e.g., dirt, soot, etc.) on a window that is used by a flame sensor in a combustion chamber setting. In one specific example, a light source, such as for example a light emitting diode (LED), can be located adjacent to a photodetector. The light source can emit light in which a first predetermined amount of the light emitted by the light source passes through the window when contamination on the window is below a threshold (e.g., no contamination or minimal contamination), and a second predetermined amount of the light reflects into the photodetector when contamination on the window is present and may be at or above the threshold. So, the amount of light that passes through depends on the amount and type of contamination.

The disclosed subject matter is described with reference to the drawings, in which like reference numerals are used to refer to like elements throughout the description. In the following detailed description, for purposes of explanation, numerous specific details are set forth in order to provide an understanding of the claimed subject matter. It will be understood, however, that the claimed subject matter can be practiced without these specific details.

Certain terminology is used herein for purposes of reference only, and thus is not intended to be limiting. For example, terms may refer to directions in the drawings or orientation of portions of a component within a consistent but arbitrary frame of reference which is made clear by reference to the text and the associated drawings describing the component under discussion. Similarly, the terms "first", "second" and other such numerical terms referring to structures or steps do not imply a sequence or order unless clearly indicated by the context.

Example embodiments that incorporate one or more aspects are described and illustrated in the drawings. These illustrated examples are not intended to be a limitation on the disclosed subject matter. For example, one or more aspects can be utilized in other embodiments and even other types of devices. Moreover, certain terminology is used herein for convenience only and is not to be taken as a limitation. Still further, in the drawings, the same reference numerals are employed for designating the same elements.

An example flame sensor, system and method of using the system, according to various aspects, are illustrated in FIGS. 1-4 and described below. FIG. 1 schematically illustrates an example flame sensor system 20 for monitoring certain characteristics of a flame 22 in a combustion system 24, for example the presence or absence of the flame. The flame 22 is located within an example combustion chamber 26 of, for example, a turbomachine, such as a gas turbine 28. The flame 22 emits electromagnetic radiation energy (e.g., light) with a characteristic, such as a hydrocarbon flame wavelength, for example in the range of about 240 nanometers (nm) to 330 nanometers (nm).

In a combustion system 24, such as the example gas turbine 28, the gas turbine can include a multitude of turbine blades (not shown) that are induced to rotate by expanding hot gases from combustion within the combustion chamber 26. The gas turbine 28 can have various, different structures and/or could be used in varied, different applications. For example, the gas turbine 28 could be constructed/configured for combustion of various fuels and used in applications such as aircraft propulsion, marine propulsion, land-based power generation, or the like. As such, it is to be appreciated that the gas turbine 28 illustrated in FIG. 1 is not intended to be limiting on further examples. Further, use of the flame sensor system 20 is not limited to use with turbines. The flame sensor system 20 may be used in other applications without limitation, such as industrial furnaces, boilers, ovens, internal combustion engines and other uses where a combustion flame is present and knowing if combustion is occurring is important.

The combustion chamber 26 is preferably located within the gas turbine 28. The combustion chamber 26 can define a substantially hollow internal region. It is to be understood that the combustion chamber 26 is generically/schematically represented in FIG. 1, and is not intended to be limiting. For instance, the generic representation of the combustion chamber 26 is intended to convey the concept that the combustion chamber can represent a number of different constructions, some of which may be generally known. Similarly, the combustion chamber 26 may be incorporated into a number of different applications and uses.

Fuel can be directed into the combustion chamber 26 to produce a relatively high-pressure, high-temperature and high-velocity gas by combustion. A fuel nozzle (not shown) can be generally provided and can deliver fuel into the combustion chamber 26. As such, the fuel nozzle can deliver the fuel into the combustion chamber 26, whereupon the fuel can be ignited with the flame 22 if a flame is present or ignited if a flame is not present, such as in a start-up cycle or flame-out condition. It is to be understood that the term "fuel" can encompass air, fuel, a mixture of both, and/or nearly any type of combustible material. It will also be appreciated that the combustion system 24 may produce combustion by-products that may collect on and contaminate components within the combustion system.

The flame sensor system 20 can also include a flame sensor 40, according to one aspect, a controller/processor 42 and a cable 44 connecting the flame sensor and controller/processor. The controller/processor 42 may be any suitable construction that can control and process electrical signals or generate an alert or alarm or otherwise communicate the condition of the combustion system 24. The controller/processor 42 may be connected, directly or indirectly, with other equipment 46 that can further process data, control the flame sensor 40 and combustion system 24, alert an operator of the condition of the flame sensor and combustion system or initiate a fuel shut-off process. The cable 44 may be of any suitable construction capable of communicating electrical signals between the flame sensor 40 and controller/processor 42, such as an electrically conductive metal wire or fiber optic cable. The controller/processor 42 may be located an appropriate distance from the flame sensor 40, connected directly to or be located within the flame sensor. The flame sensor system 20 may also include a remote processor 48 that can process data from the flame sensor 40 and amplify electrical signals.

The flame sensor 40 can be attached to the combustion system 24 so that the flame sensor can continually be in visual communication with the combustion chamber 26. An opening (not shown) is provided in an outer wall of the combustion chamber 26. The opening extends completely through the outer wall of the combustion system 24. Thus, an interior of the combustion chamber 26 is optically exposed to a location that is external to the combustion chamber. The opening can be positioned in near proximity to the flame 22, such that the opening defines an optical path through the opening from the flame.

The flame sensor 40 can be located any appropriate distance from the combustion chamber 26, for example about 152.4 millimeters (6 inches) away from the combustion chamber, though larger or smaller distances are contemplated (e.g., in the range of 1 cm to 5 meters). By being spaced away from the combustion chamber 26, the flame sensor 40 can be subject to relatively lower temperatures than it would be if it was located closer. For instance, the temperature at an end portion of the flame sensor 40 closest to the flame 22 could be in a range of about 55° C. to about 371° C. The temperature can be generally lower at a downstream location of the flame sensor 40 where electronic components are typically located, such as in the range of about 55° to about 200°.

Figure 2:
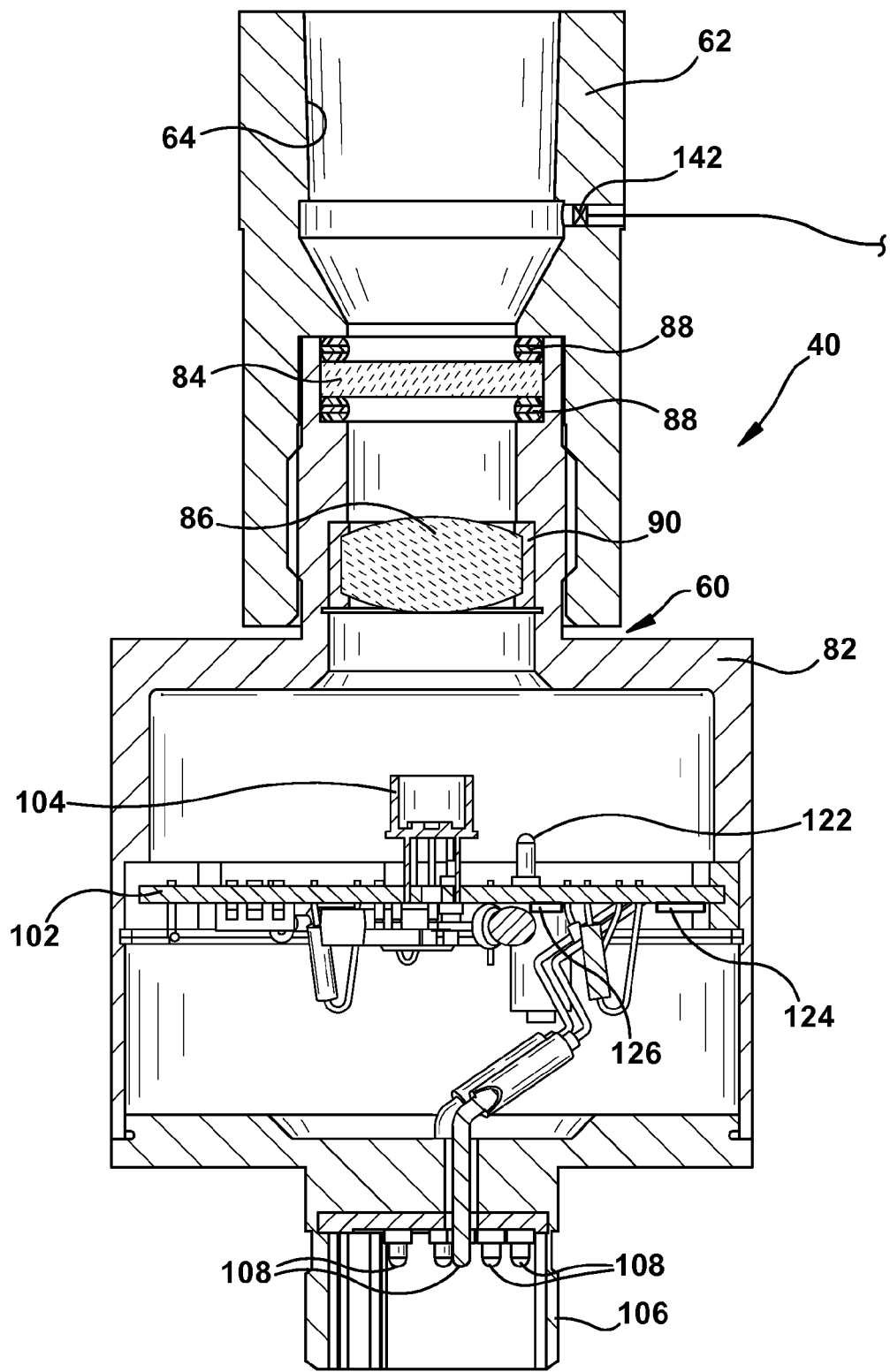
FIG. 2 is an enlarged cross-sectional view of the flame sensor illustrated in FIG. 1.

The flame sensor 40 can include a body 60 (FIG. 2). A neck 62 can have a hollow internal bore 64 with an internally threaded portion (not shown) and can be connected at one end portion to the body 60 of the flame sensor 40. The neck 62 can also be attached at an opposite end portion to a sight tube that is in communication with the combustion chamber 26 by the internally threaded portion. The sight tube can be attached, by a flange in a suitable manner, such as by mechanical fasteners, to the combustion system 24. The neck 62 can be located in the optical path from the flame 22.

The neck 62 may be attachable with the opening, such that an interior of the combustion chamber 26 is optically exposed to the internal bore 64 of the neck 62. In operation, the internal bore 64 of the neck 62 may be aligned with the opening in the outer wall of the combustion chamber 26, such that the neck 62 defines a portion of an optical path into the interior area of the combustion chamber 26. The neck 62 can be aligned with the flame 22, thus allowing for electromagnetic radiation energy EF (FIG. 3) from the light emitted by the flame 22 to propagate through the internal bore 64 of the neck 62.

The body 60 of the flame sensor 40 can also include a base 82. The neck 62 may be attached to the base 82 by suitable structure, such as threads. The flame sensor 40 can carry a sapphire window 84 and a lens 86. The window 84 can be supported in the base 82 by one or more shock absorbing and heat resistant compressible seals 88. The body 60 of the flame sensor 40 can be constructed of a number of suitable materials, including relatively high temperature materials that can withstand the aforementioned temperatures associated with the combustion process. In further examples, the body 60 of the flame sensor 40 could be constructed of materials that can withstand even higher temperatures than described herein. The body 60 of the flame sensor 40 can be formed of any number of metal-like materials that may be resistant to corrosion. In some examples, the material for the body 60 of the flame sensor 40 can include 304 stainless steel, 316 stainless steel, or the like.

The window 84 can be positioned within a groove formed in an end surface of the base 82. The groove can extend circumferentially around the internal surface of the base 82. The window 84 may have an outer diameter that is slightly smaller than the inner diameter of the groove, such that the window closely fits within the groove. It is to be understood that the groove and the window 84 are not limited to the size and shape in the illustrated example.

The sealing washers 88 can also form a seal with the window 84 and the body 60 of the flame sensor 40. In this example, the window 84 and sealing washers 88 can form a seal that forms a pressure barrier. For instance, the window 84 and sealing washers 88 can withstand gas temperatures of a relatively high temperature, such as in the range of about 2250° F., and pressures reaching about 400 lbs/in$^2$. However, it is to be understood that a variety of different windows 84 and sealing washers 88 could be implemented in the flame sensor 40 that can withstand higher or lower temperatures and pressures. In one example, however, the window 84 and sealing washers 88 can, together, function as a protective sealing barrier that separates an upstream volume (i.e., from the combustion chamber 26 to the window 84) from a downstream volume (inwardly from the window 84). Accordingly, in this example, the window 84 and sealing washers 88 can function to shield and/or protect the downstream volume within the base 82 from the relatively high temperature and pressure in the combustion chamber 26.

Further downstream from the window 84, the lens 86 may be supported in the base 82 by an elastomeric gasket 90. The lens 86 can be oriented substantially perpendicularly with respect to the longitudinal axis of the body 60 of the flame sensor 40, such that the lens 86 extends radially across the base 82. The lens 86 can include any suitable type of lens, such as a biconvex lens, planar-convex lens, or the like. Furthermore, the lens 86 can be a fused silica lens. The lens 86 can be formed of a number of different materials, however, that can withstand the relatively high temperature, pressure, and vibratory environment that the flame sensor 40 can encounter. The lens 86 can focus the electromagnetic radiation energy EF from the light emitted by the flame 22.

The flame sensor 40 can include a printed circuit board 102 supported in the base 82 by an elastomeric gasket. The printed circuit board 102 can support a photodetector 104, such as a photodiode. The base 82 of the flame sensor 40 can also include a connecting portion 106. The connecting portion 106 may have several connector pins 108 for connection to the cable 44 in order to communicate electrical signals from the flame sensor 40.

The photodetector 104 may be of the silicon carbide (SiC) photodiode type that is responsive to an electromagnetic radiation EF characteristic or wavelength that is emitted by light from the flame 22. For example, the photodetector 104 can be responsive to ultraviolet (UV) light spectrum in the range of about 200 nanometers (nm) to 400 nanometers (nm). The photodetector 104 may be responsive to electromagnetic radiation in a range that includes the wavelengths emitted by the light from the flame 22 to generate an electrical signal proportional to an intensity of the light emitted from the flame 22 that is received by the photodetector 104.

The photodetector 104 can receive the electromagnetic radiation energy EF and EFA (FIGS. 3 and 4) from the light emitted by the flame 22 and can generate a current output signal, such as a photocurrent, as a function of the electromagnetic radiation energy EF, EFA from the light emitted by the flame 22 received. The photodetector 104 can generate a photocurrent that is proportional to the intensity level of the electromagnetic radiation energy EF, EFA from the light emitted by the flame 22 that is received within the specific UV wavelength range or spectral bandwidth of the photodetector 104. For instance, the photodetector 104 can have a response in a range of from about 200 nanometers (nm) to about 400 nanometers (nm). As such, the photodetector 104 has a relatively broad spectral response that covers a 310 nm peak generally associated with the flame 22, thus allowing for a relatively reliable detection of the 310 nm emission of the flame 22. By having a high end spectral response cutoff (400 nm in this example), the photodetector 104 may ignore potential interfering blackbody radiation from interior surfaces of the combustion chamber 26.

As is generally known, the photodetector 104 can include an amplifier circuit carried on the printed circuit board 102. The photodetector 104 may generate a photocurrent that is proportional to the ultraviolet light intensity that the photodetector 104 receives. The photocurrent from the photodetector 104 can be processed and amplified by signal circuitry to produce an electrical signal. For instance, in one example, the photodetector 104 can convert electromagnetic radiation energy to an electrical signal in the form of a photocurrent. As is generally known, the photocurrent may be amplified, such that after amplification, the photocurrent is converted into a current in the range of about 4 milliamperes (mA) to about 20 milliamperes. This current can be communicated to the controller/processor 42.

This electrical signal in the form of a current can be indicative of the specific characteristics of the flame 22. The specific characteristics of the flame 22 can include, for example, the presence or absence of the flame 22 within the combustion chamber 26 or quality of combustion. For instance, in the event of a flame-out condition wherein the flame 22 has been extinguished, the absence of electromagnetic radiation energy at the photodetector 104 can be detected. This absence of electromagnetic radiation energy can cause the photodetector 104 to provide an electrical signal in the form of a photocurrent that is low or zero. In one example, this electrical signal can be sent to the controller/processor 42 and then to a fuel control apparatus, or the like, that can reduce and/or stop the supply of fuel into the combustion chamber 26. As such, the electrical signal from the photodetector 104 can be used to control the supply of fuel into the combustion chamber 26.

When the flame 22 is present within the combustion chamber 26, the presence of electromagnetic radiation energy EF from the light emitted by the flame 22 at the photodetector 104 can be detected. This electromagnetic radiation energy from the light emitted by the flame 22 can cause the photodetector 104 to provide an electrical signal in the form of a photocurrent that is proportional to the intensity of electromagnetic radiation energy EF from the light emitted by the flame. This electrical signal can be sent to the controller/processor 42 to indicate the presence of the flame 22 in the combustion chamber 26.

Figure 3:
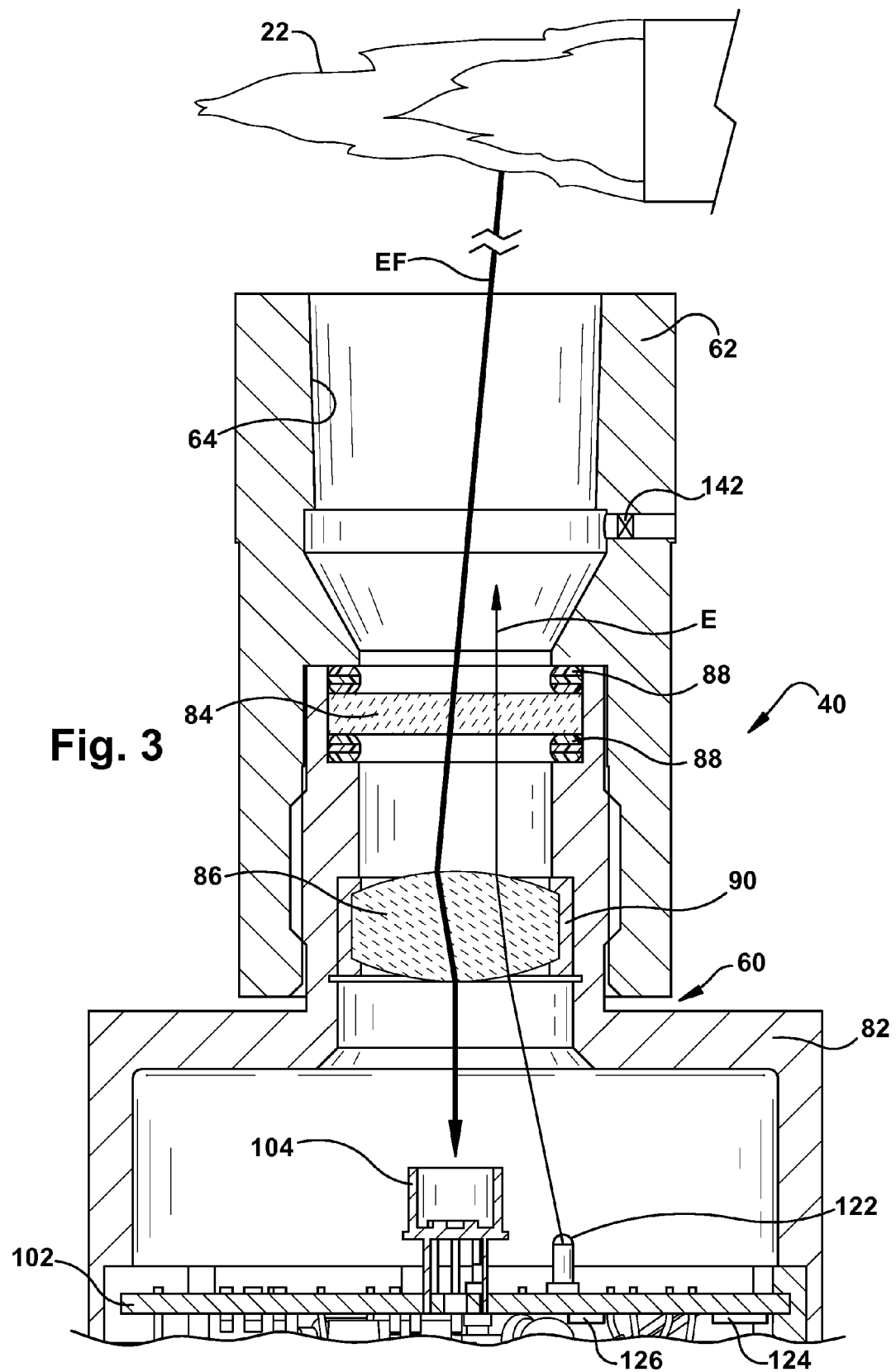
FIG. 3 is an enlarged cross-sectional view of an example portion of the flame sensor of FIG. 2, illustrating operation of a contamination detection feature of the flame sensor when there is little or no contamination of a window of the flame sensor.
Figure 4:
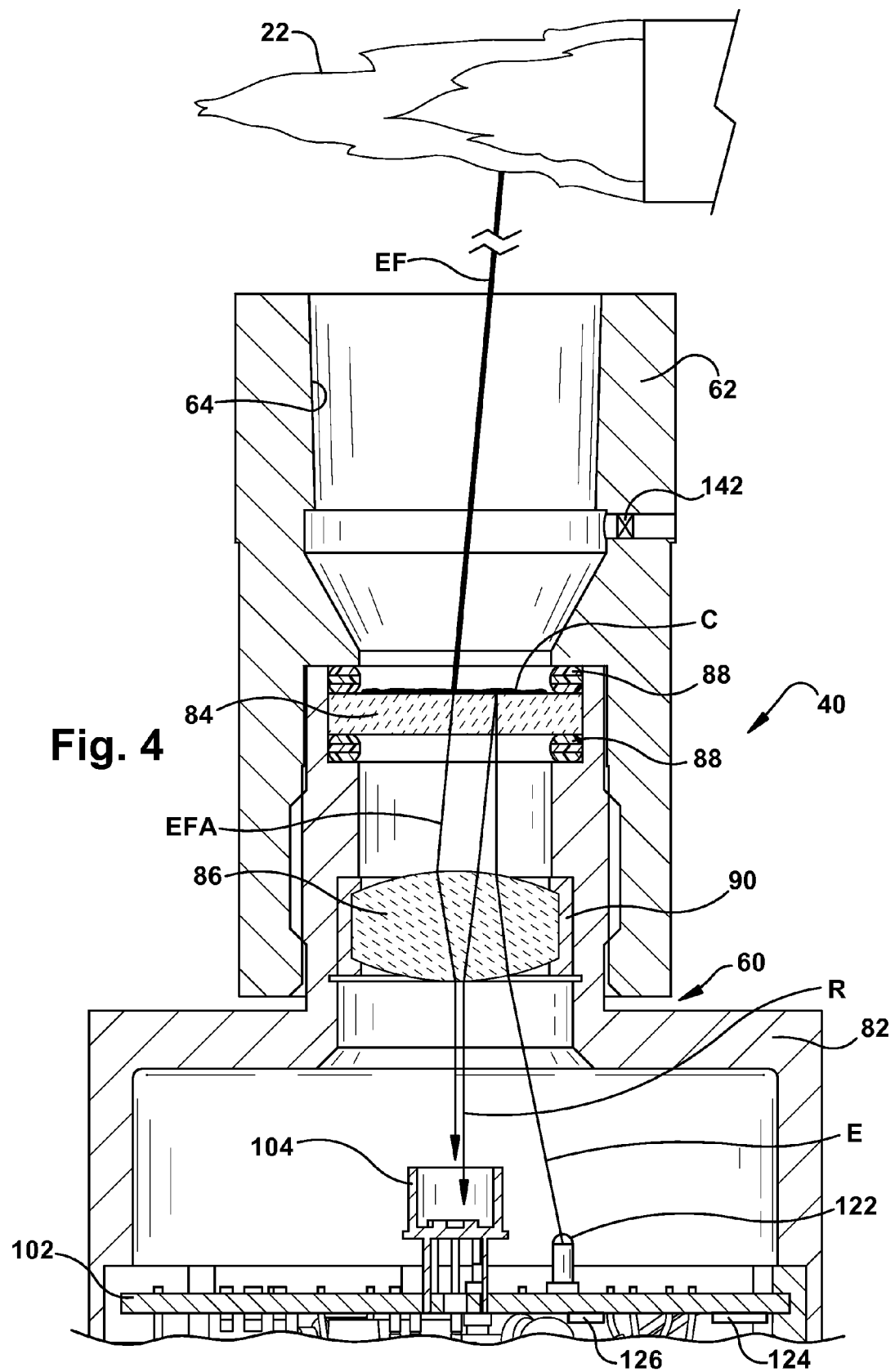
FIG. 4 is a view similar to FIG. 3, illustrating operation of the contamination detection feature of the flame sensor when there is contamination of the window of the flame sensor.

A light source 122, such as for example a light emitting diode (LED), is also supported on the printed circuit board 102 adjacent the photodetector 104. The light source 122 emits light in which a first predetermined amount of the light E emitted by the light source passes through the window 84, as illustrated in FIG. 3, when contamination C on the window is below a threshold, such as no contamination or minimal contamination. A second predetermined amount of the light R emitted by the light source 122 reflects into the photodetector 104, as illustrated in FIG. 4, when contamination C on the window 84 is present and may be at or above the threshold. The flame sensor 40 generates a signal indicative of the contamination C present on the window. It will be apparent that less than the entire amount of light E emitted by the light source 122 is necessarily reflected back into the base 82 of the flame sensor 40. A portion of the light E emitted by the light source 122 may pass through the contamination C on the window 84 and the amount that passes through depends on the amount and type of contamination. The printed circuit board 102 may also support a processor 124 and memory 126 if on-board processing of the electrical signal generated by the photodetector 104.

For example, the light source 122 may emit light E with a second characteristic or second wavelength that is distinguishable from the light EF emitted by the flame 22. The second characteristic or second wavelength may still be within the range that the photodetector 104 is capable of detecting. The light source 122 may emits light E so a first predetermined amount of the light emitted by the light source passes through the window 84 when contamination C on the window is none, little or below the threshold. A second predetermined amount of the light R emitted by the light source may reflect into the photodetector 104 when contamination C on the window 84 is at or above the threshold so the photodetector can generate a signal indicative of contamination being present on the window. The signal may be indicative of the amount of contamination C or just that contamination is present so that the light EF from the flame is attenuated to a reduced amount EFA. It is important to distinguish between contamination C on the window 84 and failure of the photodetector 104 or a flame out condition in the combustion chamber 26.

Contamination C on the window 84 of the flame sensor 40 can generally decrease sensitivity of the flame sensor by attenuating the amount of light EF emitted by the flame 22 that the photodetector 104 is exposed to. Thus, the light source 122 can generate light E using an LED or other light source to generate light inside the flame sensor 40. Contamination C of the window 84 can be detected by the photodetector 104 of the flame sensor 40 by at least a portion of the light E emitted by the light source 122 being prevented from passing through the window by the contamination. Contamination may increase the portion of the light R that is reflected back and sensed by the photodetector 104.

The light source 122 can emit light E that reaches the window 84. With no contamination on the window 84, a relatively small fraction of the light E from the light source 122 that strikes the window may be reflected back and the remaining fraction can pass through the window. The amount of light R that reflects off an uncontaminated window 84 can be referred to as the baseline reflected light. As increasing amounts of contamination C collect on the outside of the window 84, the amount of light R reflected back from the window can increase above the baseline reflected light. The amount of reflected light R above baseline reflected light can be proportional to the amount of contamination and can be reported as an indication of contamination C on the outside of the window 84.

Light from the flame 22 can flicker at multiple frequencies simultaneously. The light from the light source 122 in the flame sensor 40 may be modulated, varied or altered in amplitude and/or frequency, in a pattern that is not found in flicker from the flame 22. The output of the photodiode 104 may then be filtered using the same modulation pattern to differentiate the combustion light EF, EFA from that of the reflected light R of the light source 122.

Normally this distinguishing or filtering process could be performed with the flame 22 off so that the only light hitting the photodetector 104 is from the reflected light R from the light source 122. It may be desirable to have the ability to distinguish or filter with the combustion system 24 operating and the flame 22 generating the electromagnetic radiation EF, EFA. An improvement to this distinguishing or filtering process can be achieved using alternating current (AC) modulation of the light source 122. For example, the pattern created by modulation of the light source 122 may be used and the data controller/processor 42 filters out light other than this modulated light from light source 122. Various other methods of modulation and filtering can be used.

The light source 122 output can be modulated by driving it with an alternating current that varies a characteristic, such as intensity of the light E emitted from the light source 122, in a predetermined pattern, frequency and/or amplitude. The photodetector 104 output signal can be filtered for the same characteristic at the predetermined pattern, frequency and/or amplitude. For example, off-data can be acquired and filtered first with the light source 122 off to measure the baseline intensity of the flame 22 at the predetermined frequency. On-data can then be acquired with the light source 122 driven by the modulator in the predetermined pattern, frequency and/or amplitude. In both cases the intensity of the light can be averaged over a predetermined time period. Since flame flicker can contain a continuous spectrum of "flicker noise", there can be a non-zero component from the flame 22 for any pattern chosen. The off-data can be subtracted from the on-data. The intensity of the result can be proportional to the amount of light reflected back from the contaminated window 84 and can be proportional to the amount of contamination C on the window.

According to another aspect, it may be desirable to distinguish the reflected portion of the light R from the light generated by the flame 22. The light source 122 can be modulated to emit light at a predetermined pattern that is different than the flicker pattern emitted by the flame 22. The predetermined pattern generated by the light source 122 may be capable of being detected by the photodetector 104. The predetermined pattern can then be filtered and distinguished from the light emitted EF, EFA by the flame 22. Thus, the reflected light R generated by the internal light source 122 can be distinguished from electromagnetic radiation EF, EFA emitted by the flame 22.

Moisture content in the combustion chamber 26 can contribute to contamination C of the window 84 or otherwise affect combustion. Thus, the flame sensor 40 may further include a humidity or moisture sensor 142. The moisture sensor 142 may be supported in the neck 62 of the flame sensor. However, it will be apparent that the moisture sensor 142 may be mounted anywhere that is suitably in communication with the combustion chamber 26. The moisture sensor 142 can be in communication with the controller/processor 42 and can continually or periodically send a signal to the controller/processor indicating the moisture content in the combustion chamber 26. A signal from the moisture sensor 142 can be digitized by the on-board processor 124 or remote processor 48 and communicated to the controller/processor 42.

The operation of the flame sensor 40, when the window 84 is not contaminated, can now be briefly described. As illustrated in FIG. 3, electromagnetic radiation energy EF from the light emitted by the flame 22 may be directed into the neck 62 before entering the base 82 of the flame sensor 40. The electromagnetic radiation energy EF from the light emitted by the flame 22 can then pass through the window 84 and through the lens 86. The lens 86 can focus the electromagnetic radiation energy EF from the light emitted by the flame 22 into the end of the photodetector 104. The photodetector 104 can detect the specific characteristics of the flame 22, such as the presence or absence of the flame. The photodetector 104 can then generate an electrical signal as a function of the intensity of the electromagnetic radiation energy from the light emitted by the flame 22. The electrical signal may then be processed by the controller/processor 42, whether the controller/processor is the on-board processor 124 located on the printed circuit board 102 or the remote controller/processor 42, as illustrated in FIG. 1.

The operation of the flame sensor 40, when the window 84 is contaminated, can now be briefly described. As illustrated in FIG. 4, electromagnetic radiation energy EF from the light emitted by the flame 22 may be directed into the neck 62 before entering the base 82 of the flame sensor 40. An attenuated portion of the electromagnetic radiation energy EFA from the light emitted by the flame 22 may then pass through the contamination C and the window 84 and through the lens 86. The lens 86 can focus the electromagnetic radiation energy EFA into the end of the photodetector 104. The photodetector 104 can detect the specific characteristics of the flame 22, such as the presence or absence of the flame. The photodetector 104 may then generate an electrical signal as a function of the intensity of the electromagnetic radiation energy EFA from the light emitted by the flame 22.

Concurrently, the light source 122 may generate light E to generate light inside the flame sensor 40. A portion of the light E emitted by the light source 122 may be prevented from passing through the window 84 by the contamination C. A portion of the light E may be reflected back as reflected light R and the reflected light is sensed by the photodetector 104. The light generated by the light source 122 can be modulated so it can be distinguished from the light EF, EFA emitted by the flame 22. The light energy from the portion of the light EFA passing through the contamination C and the modulated reflected light R can then be filtered and further processed by the controller/processor 42. The filtered and processed signal can be used for numerous purposes including indicating the presence of a flame 22 in the combustion chamber 26 and/or if the window 84 is contaminated.

Referring now to FIG. 1, operation of the flame sensor system 20 can be described in more detail. Fuel can be provided to the combustion chamber 26 through the fuel nozzle to produce the flame 22. The flame sensor 40 can be attached in visual communication with the combustion chamber 26, such that the flame sensor 40 is spaced a desired distance away from the flame 22. Electromagnetic radiation energy EF, indicative of the specific characteristics of the flame 22, may be conveyed from the flame in the combustion chamber 26, through the neck 62 and into the base 82 of the flame sensor 40. Once in the flame sensor 40, the electromagnetic radiation energy EF, EFA can pass through the window 84 and can be focused by the lens 86 (shown in FIGS. 3 and 4) onto the photodetector 104.

The photodetector 104 can sense the specific characteristics of the flame 22, such as the presence or absence of the flame. The photodetector 104 then can generate an electrical signal as a function of the intensity of the electromagnetic radiation energy EF, EFA generated by the flame 22. When the window 84 is contaminated, as illustrated in FIG. 4, an attenuated portion of the electromagnetic radiation energy EFA can then pass through contamination C and the window 84 and through the lens 86. The lens 86 can focus the electromagnetic radiation energy EFA into the end of the photodetector 104. The photodetector 104 can sense the specific characteristics of the flame 22, such as the presence or absence of the flame. The photodetector 104 then can generate an electrical signal as a function of the intensity of the electromagnetic radiation energy EFA generated by the flame 22. The signal indicative of contamination C on the window 84 can represent the amount of contamination on the window as a function of the amount or intensity of light R from the light source that is reflected into the photodetector 104.

The light source 122 can generate light E inside the flame sensor 40. A portion of the light E emitted by the light source 122 may be prevented from passing through the window 84 by the contamination C. A portion of the light E may be reflected back as reflected light R and the reflected light may be sensed by the photodetector 104. The light generated by the light source 122 can be modulated so it can be distinguished from the light emitted EF, EFA emitted by the flame 22. The light energy from the portion of the light EFA passing through the contamination C and the reflected light R can then be filtered and further processed by the controller/processor 42. The filtered and processed signal can be used for numerous purposes including but not limited to, indicating the presence or absence of a flame 22 in the combustion chamber 26 and/or if the window 84 is contaminated. The controller/processor 42 can communicate the characteristics of the flame 22 and contamination C of the window 84 by various visual or auditory alerts or alarms, as is known. Adjustments to the fuel delivery system can be made as a function of the condition of the flame 22.

The disclosed subject matter has been described with reference to the example embodiments described above. Modifications and alterations will occur to others upon a reading and understanding of this specification. Example embodiments incorporating one or more aspects of the disclosed subject matter are intended to include all such modifications and alterations insofar as they come within the scope of the appended claims.

When introducing elements or features of the present disclosure and the exemplary aspects, the articles "a", "an" and "the" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

From the above description of at least one aspect, those skilled in the art will perceive improvements, changes and modifications. Such improvements, changes and modifications within the skill of the art are intended to be covered by the appended claims.

Although the description has been shown and described with respect to one or more embodiments, aspects, applications or implementations, it will occur to those skilled in the art based upon a reading and understanding of this description and the drawings that equivalent alterations and modifications may be made without detracting from the spirit and scope of the embodiments, aspects or implementations in the description. The description and claims are intended to include all such modifications and alterations.

What is claimed is:

1. A flame sensor for detecting the presence of a flame in a combustion system in which the flame emits electromagnetic radiation, the flame sensor comprising:
    a body disposed proximate to the combustion system;
    a photodetector supported in the body, the photodetector configured to generate an electrical signal proportional to an intensity of electromagnetic radiation;
    a window supported in the body and located between the combustion system and the photodetector;
    a source supported in the body, the source emitting electromagnetic radiation toward the window, wherein the source and photodetector being positioned adjacent each other such that at least some of the electromagnetic radiation emitted by the source reflects back from contamination present on the window toward the photodetector when contamination is present on the window; and
    a modulator that modulates the electromagnetic radiation emitted by the source, wherein the modulator is configured to modulate the source by varying an emission intensity of electromagnetic radiation emitted by the source according to a predetermined pattern that is different than a flicker pattern emitted by the flame.

2. The flame sensor of claim 1 wherein the photodetector is further configured to distinguish the electromagnetic radiation emitted by the flame from the electromagnetic radiation emitted by the source using the modulation.

3. The flame sensor of claim 1 further including a processor configured to filter the pattern of the electromagnetic radiation emitted by the source from the electromagnetic radiation emitted by the flame to determine the amount of electromagnetic radiation emitted by the source reflected into the photodetector.

4. The flame sensor of claim 1 wherein the source is configured to emit electromagnetic radiation within a range of wavelengths that the photodetector is capable of detecting.

5. The flame sensor of claim 1 wherein the photodetector is configured to detect the electromagnetic radiation emitted by the flame in an ultraviolet range of wavelengths.

6. The flame sensor of claim 1 further including a moisture sensor configured to indicate the presence of moisture within the combustion system.

7. The flame sensor of claim 1 further including a circuit board configured to support the photodetector and the source.

8. The flame sensor of claim 1 wherein the photodetector is configured to differentiate between electromagnetic radiation emitted by the flame and electromagnetic radiation emitted by the source.

9. A system comprising:
    a combustion source in which a flame may be generated and in which the flame emits electromagnetic radiation;
    a sensor for detecting the presence of the flame in the combustion source, the flame sensor comprising:
    a body disposed proximate to the combustion system;
    a photodetector supported in the body, the photodetector configured to generate an electrical signal proportional to an intensity of electromagnetic radiation;
    a window supported in the body and located between the combustion system and the photodetector; and
    a source supported in the body, the source emitting electromagnetic radiation toward the window, wherein the source and photodetector being positioned adjacent each other such that at least some of the electromagnetic radiation emitted by the source reflects back from contamination present on the window toward the photodetector when contamination is present on the window; and a modulator to modulate the source by varying an emission intensity of the electromagnetic radiation emitted by the source to a predetermined pattern that is different than a flicker pattern emitted by the flame so the electromagnetic radiation sensed by the photodetector can be distinguished between the electromagnetic radiation emitted by the source and the electromagnetic radiation emitted by the flame.

10. The system of claim 9 further including a processor configured to filter the pattern of the electromagnetic radiation emitted by the source from the electromagnetic radiation emitted by the flame to determine the amount of electromagnetic radiation emitted by the source reflected into the photodetector.

11. The system of claim 9 further including a processor configured to determine the amount of electromagnetic radiation emitted by the source reflected into the photodetector at a predetermined time.

12. The system of claim 9 further including a moisture sensor configured to indicate the presence of moisture within the combustion system.

13. The system of claim 9 wherein the photodetector is configured to detect the electromagnetic radiation emitted by the flame in an ultraviolet range of wavelengths.

14. The system of claim 9 further including circuit board configured to support the photodetector and the source.

15. A method of detecting contamination on a flame sensor window, the method comprising the steps of:

providing a flame sensor for detecting the presence of a flame in a combustion system in which the flame emits electromagnetic radiation, the flame sensor including a body disposed proximate to the combustion system;

supporting a photodetector in the body, the photodetector detecting the electromagnetic radiation emitted by the flame, the photodetector configured to generate an electrical signal proportional to an intensity of the electromagnetic radiation;

supporting a window in the body and locating the window between the combustion system and the photodetector;

supporting a source in the body at a position adjacent to the photodetector, the source emitting electromagnetic radiation toward the window;

passing a first predetermined amount of the electromagnetic radiation emitted by the source through the window when there is no contamination on the window;

reflecting, from contamination present on the window a second predetermined amount of the electromagnetic radiation emitted by the source in a direction towards the photodetector when there is contamination on the window;

detecting with the photodetector the second predetermined amount of the electromagnetic radiation emitted by the source, and reflected from contamination present on the window, and communicating a signal indicative of contamination on the window; and modulating the source by varying an emission intensity of the electromagnetic radiation emitted by the source in a predetermined pattern that is different than a flicker pattern emitted by the flame so the electromagnetic radiation sensed by the photodetector can be distinguished between the electromagnetic radiation emitted by the source and the electromagnetic radiation emitted by the flame.

16. The method of claim 15 further including the step of providing a moisture sensor configured to indicate the presence of moisture within the combustion system.

17. The method of claim 15 further including the step of detecting with the photodetector electromagnetic radiation emitted from the flame in the ultraviolet range.

18. The method of claim 15 further including the step of processing the signal to determine the amount of electromagnetic radiation emitted by the source reflected into the photodetector at a predetermined time.

* * * * *